United States Patent
Alla et al.

(10) Patent No.: US 11,028,044 B2
(45) Date of Patent: Jun. 8, 2021

(54) VERSATILE, CONCISE AND CONVENIENT PROCESS FOR THE COMMERCIAL SCALE PREPARATION OF HIGHEST PURE 3,3'5,5'-TETRAMETHYLBENZIDINE (TMB) AND ITS SALTS, A CHROMOGENIC SUBSTRATE USED IN STAINING PROCEDURES IN IMMUNOHISTOCHEMISTRY AND VISUALIZING REAGENT IN ENZYME-LINKED IMMUNOSORBENT ASSAYS

(71) Applicants: Sekar Reddy Alla, Burlington, MA (US); Rahul R. Alla, Burlington, MA (US); Rupini Alla, Royal Oak, MI (US)

(72) Inventors: Sekar Reddy Alla, Burlington, MA (US); Rahul R. Alla, Burlington, MA (US); Rupini Alla, Royal Oak, MI (US)

(73) Assignee: SLR Biosciences, LLC, Burlington, MA (US)

( * ) Notice: Subject to any disclaimer, the term of this patent is extended or adjusted under 35 U.S.C. 154(b) by 0 days.

(21) Appl. No.: 16/654,814

(22) Filed: Oct. 16, 2019

(65) Prior Publication Data

US 2021/0114974 A1    Apr. 22, 2021

(51) Int. Cl.
*C07C 245/08*    (2006.01)

(52) U.S. Cl.
CPC .................................. *C07C 245/08* (2013.01)

(58) Field of Classification Search
CPC ...................................................... C07C 245/08
USPC ......................................................... 534/572
See application file for complete search history.

(56) References Cited

FOREIGN PATENT DOCUMENTS

CN        108997139 A    * 12/2018

* cited by examiner

*Primary Examiner* — Kristin A Vajda

(57) ABSTRACT

The present invention relates to a process for the preparation of 3,3',5,5'-Tetramethylbenzidine represented by formula I, and processes for the preparation of intermediates used in the preparation of 3,3',5,5'-Tetramethylbenzidine.

3 Claims, 4 Drawing Sheets

FIG. 1  1HNMR SPECTRAM IN CDCl3

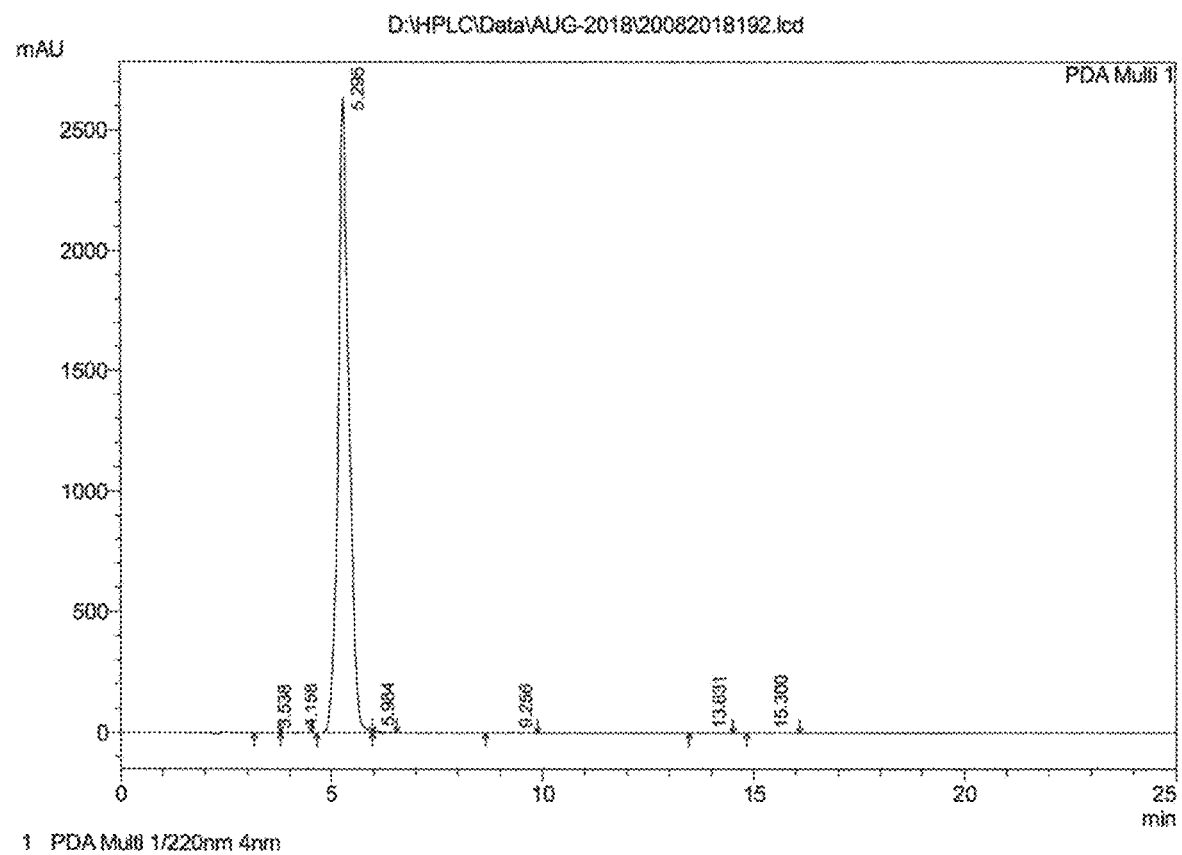
FIG. 3    HPLC

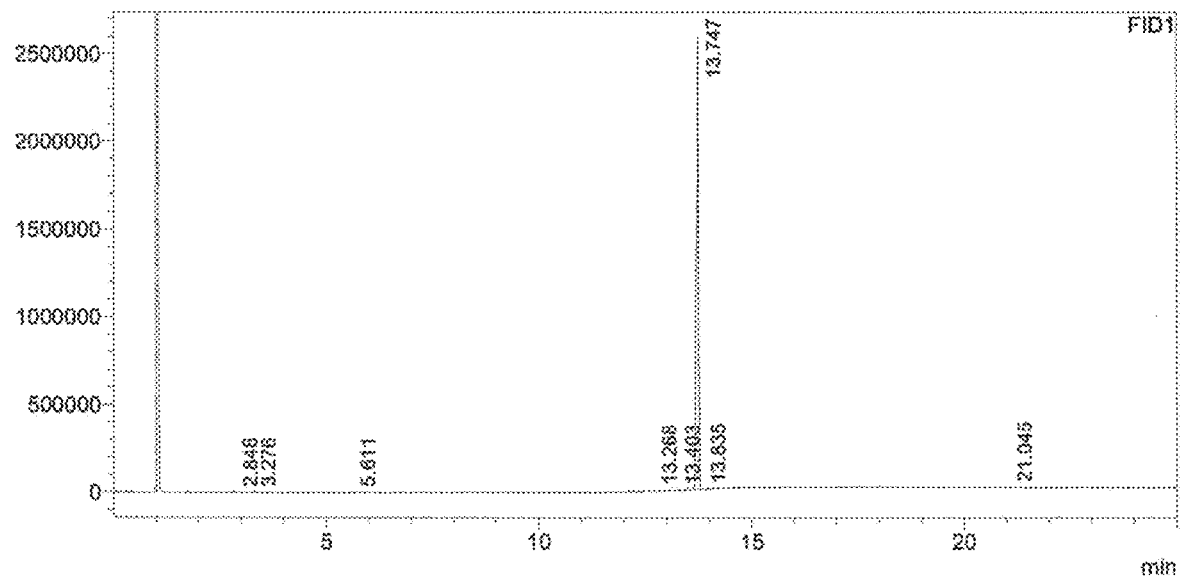
<Peak Table>
FID1
| Peak# | Ret. Time | Area | Height | Area% | Name |
|---|---|---|---|---|---|
| 1 | 2.848 | 1598 | 373 | 0.019 | |
| 2 | 3.276 | 3330 | 820 | 0.039 | |
| 3 | 5.611 | 6338 | 2099 | 0.075 | |
| 4 | 13.268 | 6573 | 3336 | 0.078 | |
| 5 | 13.403 | 2012 | 917 | 0.024 | |
| 6 | 13.747 | 8431981 | 2575882 | 99.629 | |
| 7 | 13.835 | 4323 | 2307 | 0.051 | |
| 8 | 21.045 | 7265 | 1252 | 0.086 | |
| Total | | 8463419 | 2586986 | 100.000 | |
FIG. 4      GAS CHROMATOGRAM (GC)

VERSATILE, CONCISE AND CONVENIENT PROCESS FOR THE COMMERCIAL SCALE PREPARATION OF HIGHEST PURE 3,3'5,5'-TETRAMETHYLBENZIDINE (TMB) AND ITS SALTS, A CHROMOGENIC SUBSTRATE USED IN STAINING PROCEDURES IN IMMUNOHISTOCHEMISTRY AND VISUALIZING REAGENT IN ENZYME-LINKED IMMUNOSORBENT ASSAYS

The present application relates to process for the preparation of TMB. The compound having the adopted name "'TMB' has a chemical name 3,3',5,5'-Tetramethylbenzidine, and is structurally represented by Formula I.

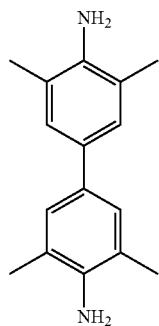

Formula I

TMB, a biphenyl derivative is a chromogenic substrate that is used in staining procedures in immunohistochemistry and is a visualizing reagent used in enzyme-linked immunosorbent assays.

The compound is commercially marketed by several companies such as Sigma-aldrich, Alfa Aesar etc. in mg to gram scale.

U.S. Pat. No. 4,022,795 discloses a process for preparing 3,3',5,5'-tetramethylbenzidine which involves reacting 4-Bromo-2,6-dimethylaniline in presence of 3% palladium on charcoal.

CN 1056304 discloses a process which involves oxidation of 2,6-dimethylaniline with potassium ferricyanide to give azobenzene and its reduction with Zn in water-ethanol followed by rearrangement with HCl to give 3,3',5,5'-tetramethylbenzidine.

CN 108997139 discloses a process for preparing 3,3',5,5'-tetramethylbenzidine and its hydrochloride salt which involves treating of 2,6-dimethylaniline with potassium permanganate in ethyl acetate followed by reaction with zinc powder and conc. sulfuric acid.

CN 106631825 discloses a process in which activated 2,6-dimethylaniline was treated with metal catalyst followed by treatment with Zn to give 3,3',5,5'-tetramethylbenzidine.

Huang, Bin et al., "Study on synthesis of 3,3',5,5'-tetramethylbenzidine" Jingxi Yu Zhuanyong Huaxuepin 19(2) pp. 17-19, 2011 discloses a process for the preparation of 3,3',5,5'-tetramethylbenzidine, which involves bromination of 2,6-dimethylaniline followed by coupling using palladium catalyst.

Even though some methods exist in literature to prepare TMB in large scale, the quality of the final product was not satisfactory for end users. This prompted us to explore and establish a simple and efficient process for the preparation of high quality TMB, which is also amenable to scaleup to meet the growing demand for the compound. The advantages of this new process include, but not limited to, improvements in safety, quality, yield, operability, scalability and efficiency.

SUMMARY OF THE INVENTION

The present invention provides, a process for the preparation of 1,2-bis(2,6-dimethylphenyl)diazene (III), which comprises reacting 2,6-dimethylaniline, of formula (II) with $KMnO_4$ in an aprotic solvent such as dialkyl ketone with a boiling point greater than about 55° C.

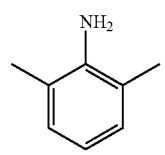

Formula (II)

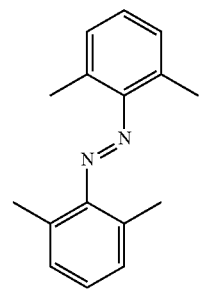

Formula (III)

The process disclosed herein provides a number of advantages over prior art processes of CN 108997139 and CN 1056304.

In one aspect, the dialkyl ketone used in the preparation of 1,2-bis(2,6-dimethylphenyl)diazene may be, for example, any analog such as acetone, butanone, methyl vinyl ketone, which has a boiling point greater than 55° C.

In a further aspect, the present invention provides a process for the preparation of TMB, the compound of formula (I), which process comprises reacting compound III in a protic solvent such as methanol with Zn and $NH_4Cl$ in water.

This two-step process may advantageously provide the compound of formula (I) in a substantially higher yield and purity than the process outlined in CN 108997139 and CN 1056304.

BRIEF DESCRIPTION OF THE DRAWINGS

FIG. 3 is HPLC of 3,3',5,5'-Tetramethylbenzidine, obtained according to Example 2

FIG. 4 is gas chromatogram of 3,3',5,5'-Tetramethylbenzidine, obtained according to Example 2

DETAILED DESCRIPTION OF THE INVENTION

Figure 1:
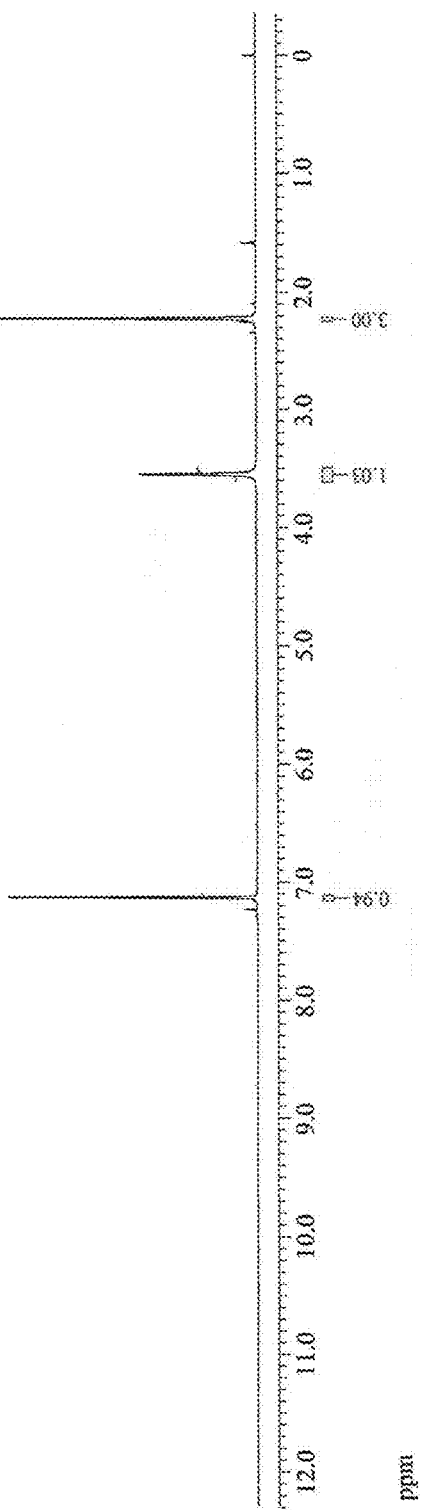
FIG. 1 is $^1HNMR$ of 3,3',5,5'-Tetramethylbenzidine, obtained according to Example 2
Figure 2:
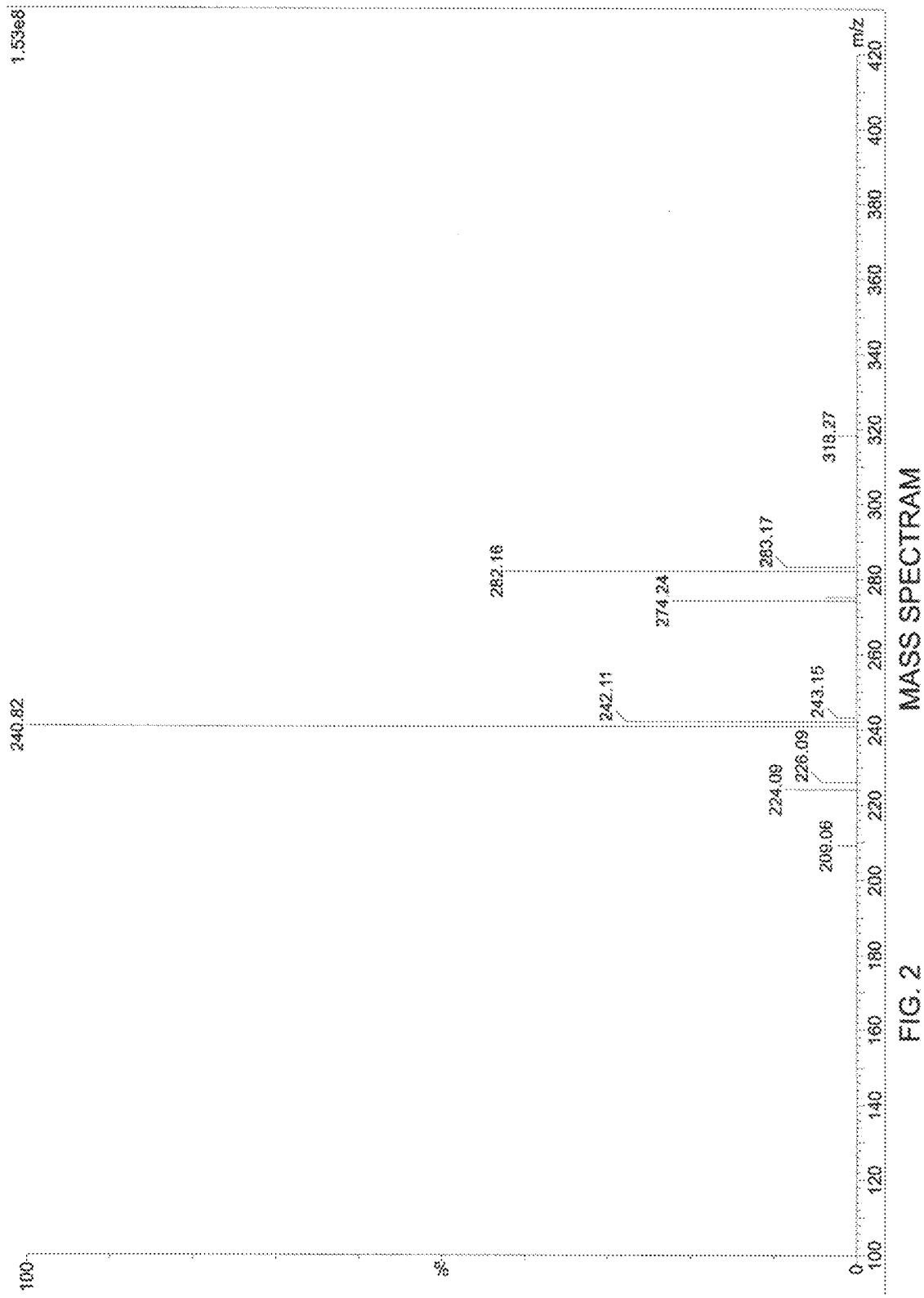
FIG. 2 is mass spectrum of 3,3',5,5'-Tetramethylbenzidine, obtained according to Example 2

The present invention provides, a process for the preparation of 3,3',5,5'-tetramethylbenzidine, which comprises (step II):

a) 1,2-bis(2,6-dimethylphenyl)diazene, of formula (III)

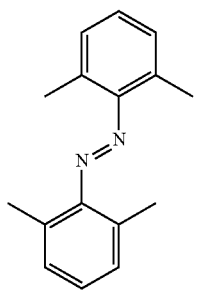

(III)

and ammonium chloride and Zinc dust in a protic solvent or a mixture of protic solvents with a boiling point greater than about 65° C.; and optionally
  b) In one aspect, the protic solvents used in the preparation of 3,3',5,5'-tetramethylbenzidine may be, for example, any isomer of butanol or propanol, water, ethanol or methanol.
    The temperature range under which step (a) is performed may be determined based on the solubility of the compound of formula (III) and the reagents used in the reaction in the selected solvents and the boiling point of said solvents. For example, reaction in methanol and water may be performed between approximately 65° C. and 100° C.
  c) Work-up and crystallization of the product of step (a).
    The product of step (a) is strategically converted into HCl or $H_2SO_4$ salt by treating it with conc. HCl or $H_2SO_4$ and then worked up as described in example 2.

In a further aspect, the present invention provides a process for the preparation of the compound of formula (III), which process comprises reacting 2,6-Dimethyl aniline with $KMnO_4$ in an aprotic solvent such as dialkyl ketone with a boiling point greater than about 55° C. (step I)
  d) In one aspect, the reaction may be performed in an aprotic solvent, which has a boiling point greater than 55° C., including but not limited to, acetone, butanone or methyl vinyl ketone.
  e) In a further aspect of the invention the step I reaction between a compound of formula (II) and $KMnO_4$ is carried out in acetone as a solvent and/or at a temperature between 0° C. and 60° C.

EXPERIMENTAL SECTION

Abbreviations $KMnO_4$: Potassium permanganate
TMB: 3,3',5,5'-Tetramethylbenzidine Example 1: Preparation of 1,2-bis(2,6-dimethylphenyl)diazene To a solution of 2,6-Dimethyl aniline (300 g) in acetone (2250 mL), $KMnO_4$ (900 g) was added in lots over a period of 4 hours at room temperature. The reaction mixture was further stirred at room temperature for 2 h, after which it was filtered over celite. The residue was washed with acetone. The filtrate was concentrated to get 1,2-bis(2,6-dimethylphenyl)diazene (205 g) as dark orange liquid.

Example 2: Preparation of 3,3',5,5'-tetramethyl benzidine

To a solution of 1,2-bis(2,6-dimethylphenyl)diazene (300 g) in methanol (1170 mL), a solution of ammonium chloride (209 g) in water (520 mL) was added, to which Zinc dust (249 g) was added over a period of 2 hours at room temperature. The reaction mixture was further stirred at reflux temperature for 4 h after which it was filtered over celite and washed with ethyl acetate (2 L) in hot condition. The filtrate was acidified using dilute HCl to a pH of 2. The salt formed was filtered and washed with ethyl acetate (1 L). The salt was basified to a pH of 12 and extracted with dichloromethane (2.5 lit). The extract was washed with brine and concentrated to get crystals of TMB. The crystals were milled and washed with 2 volumes of diethyl ether to get TMB as off white solid (85 gm) with 99.6% purity by HPLC and GC.

MS (m/z): 240.82 (M+H$^+$); $^1$H NMR (500 MHz; CDCl$_3$): 7.13 (4H, s), 3.55 (4H, s), 2.22 (12H, s).

INSTRUMENT PARAMETERS $^1$H NMR spectra were recorded on a Jeol, 500 MHz instrument in Chloroform-D
HPLC Conditions:
Column: 250×4.6 mm, 5μ, Waters (C18)
Mobile Phase: 10 mM Ammonium acetate buffer: Methanol (30:70)
Linear Isocratic method over 25 mins.
Total Run Time: 25 minutes.
Flow Rate: 1.0 ml/min
Column Temperature: 25° C.

The invention claimed is:
1. A process for the preparation of 1,2-bis(2,6-dimethylphenyl)diazene (III), which comprises reacting 2,6-dimethylaniline of Formula (II) with KMnO4 in an aprotic solvent dialkyl ketone with a boiling point greater than about 55° C.; wherein Formula (II) is

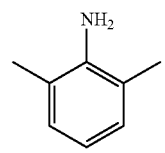

and Formula (III) is

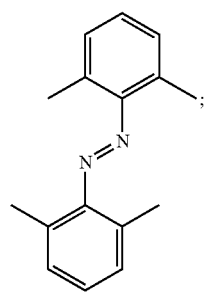

and wherein the solvent is acetone and the reaction temperature is between 0° C. and 60° C.
2. The process according to claim 1, wherein the compound of Formula (III) is further treated with ammonium chloride and zinc dust in a suitable solvent; wherein the solvent is a mixture of methanol and water and the resulting product in treated with conc. HCl or $H_2SO_4$.

3. The process according to claim 2, which is performed sequentially after a process for the preparation of 1,2-bis(2,6-dimethylphenyl)diazene (III).

\* \* \* \* \*